United States Patent [19]

Cruzan

[11] 4,036,062
[45] July 19, 1977

[54] SAMPLE DILUTION

[75] Inventor: Charles G. Cruzan, Bartlesville, Okla.

[73] Assignee: Phillips Petroleum Company, Bartlesville, Okla.

[21] Appl. No.: 719,216

[22] Filed: Aug. 31, 1976

[51] Int. Cl.² .............................................. G01N 1/10
[52] U.S. Cl. .............................. 73/422 GC; 137/604; 259/4 AB
[58] Field of Search ................ 73/23.1, 61.1, 422 GC; 137/604; 259/4

[56] References Cited

U.S. PATENT DOCUMENTS

| 866,122 | 9/1907 | Foster | 137/637.1 |
|---|---|---|---|
| 3,066,474 | 10/1961 | Fitch | 58/28 |
| 3,273,377 | 9/1966 | Testerman et al. | 73/23.1 |
| 3,325,150 | 6/1967 | Broders | 259/4 |
| 3,868,967 | 3/1975 | Harding | 137/604 |

FOREIGN PATENT DOCUMENTS

| 811,973 | 5/1969 | Canada | 73/1 G |

OTHER PUBLICATIONS

SAE Journal, Aug. 1967, v. 75, pp. 36–38.
Control Engineering, Sept. 1973, Andreier, pp. 56–57.
Instruments and Control Systems, June 1970, vol. 43, No. 6, Campagnuolo et al., pp. 99–103.
Instruments and Control Systems, April 1972, vol. 45, No. 4, pp. 57–59.

*Primary Examiner*—S. Clement Swisher

[57] ABSTRACT

Two conduit means having a preselected volumetric relationship one to the other, at least one of these conduit means having a fluid oscillator means forming at least a portion thereof, are utilized in the dilution of a sample by filling one of the conduit means with a diluent liquid and the other with a sample material, then connecting the two conduit means together in a closed conduit loop and circulating the contents of the loop through the loop in order to cause uniform mixing of the sample material with the diluent liquid. In a preferred embodiment the diluted sample material is resampled from the conduit loop for further use or analysis.

18 Claims, 4 Drawing Figures

SAMPLE DILUTION

This invention relates to an apparatus and method for diluting a sample. In another aspect the invention relates to an apparatus and method for diluting a sample material using a fluid oscillator means to produce fluid oscillation. In yet another aspect the invention relates to an apparatus and method for automatic dilution of a sample material. In still another aspect the invention relates to an apparatus and method for diluting a sample by continuously circulating preselected volumes of sample material and diluent liquid around a closed conduit loop containing a fluid oscillator means to produce fluid oscillation. In another aspect, the invention relates to an apparatus and method for diluting a sample which provide for a determination of the relative density of the material at a preselected location within the dilution system.

Samples to be analyzed, particularly those to be analyzed by process liquid chromatography or laboratory liquid chromatography often require dilution prior to analysis. Dilution is ordinarily used to regulate some property of the sample mixture to aid the analysis. For example, the boiling point of the sample can be regulated to prevent solidification or vaporization, the total quantity used for analysis of the sample can be reduced to below the normally available by using a sample injection valve alone, or the viscosity of the sample can be reduced to provide better sample flow through the analysis instrument. In addition to dilution of samples to be analyzed by liquid chromatography, dilution of samples for other purposes is likewise often desirable.

It is particularly desirable to provide an automatic sample dilution system suitable for use with high viscosity samples such as polymers or rubbers which either cannot be analyzed by liquid chromatography in an undiluted state or which require extremely high temperature analyzer operation in order to permit analysis without dilution.

Accordingly, an object of the invention is to provide an apparatus and method for diluting a sample. Another object of the invention is to provide an apparatus and method for diluting a sample material using a fluid oscillator means. Yet another object of the invention is to provide an apparatus and method for automatic dilution of a sample material. Still another object of the invention is to provide an apparatus and method for diluting a sample by continuously circulating preselected volumes of sample material and diluent liquid around a closed circuit loop containing a fluid oscillator means. Another object of the invention is to provide an apparatus and method for diluting high viscosity samples. An additional object of the invention is to provide an apparatus and method for diluting a sample which provides for a determination of the relative density of the material at a preselected location within the dilution system.

In accordance with the invention an apparatus and method are provided whereby a first conduit means having a first volume is filled with a diluent liquid and a second conduit means having a volume bearing a predetermined size relationship to the volume of the first conduit means is filled with a sample material. At least one of the first and second conduit means has as a part thereof a fluid oscillator means for imparting flow oscillation to at least a portion of the fluid passing therethrough. The first and second conduit means are then connected in series to form a closed conduit loop and the contents of the conduit loop are circulated around the loop to cause mixing of the diluent liquid and sample material. The diluted sample material in the conduit loop can then be resampled for analysis or for any other purpose for which a diluted sample is desired. After the desired use is made of the diluted sample material the first and second conduit means can be returned to their initial condition so that diluent liquid can be flushed through the first conduit means and sample material can be flushed through the second conduit means in order to obtain fresh diluent liquid and sample material for use in a subsequent dilution procedure. Sensing of the frequency of oscillation during the dilution process and during the flushing and refilling of the conduit means containing the fluid oscillator means can be used to determine the relative density of the material passing through the fluid oscillator and thus determine whether dilution or flushing is complete.

Additional objects and advantages of the invention will be apparent from the description thereof and the appended claims thereto, as well as from the detailed description of the drawing in which:

Figure 1:
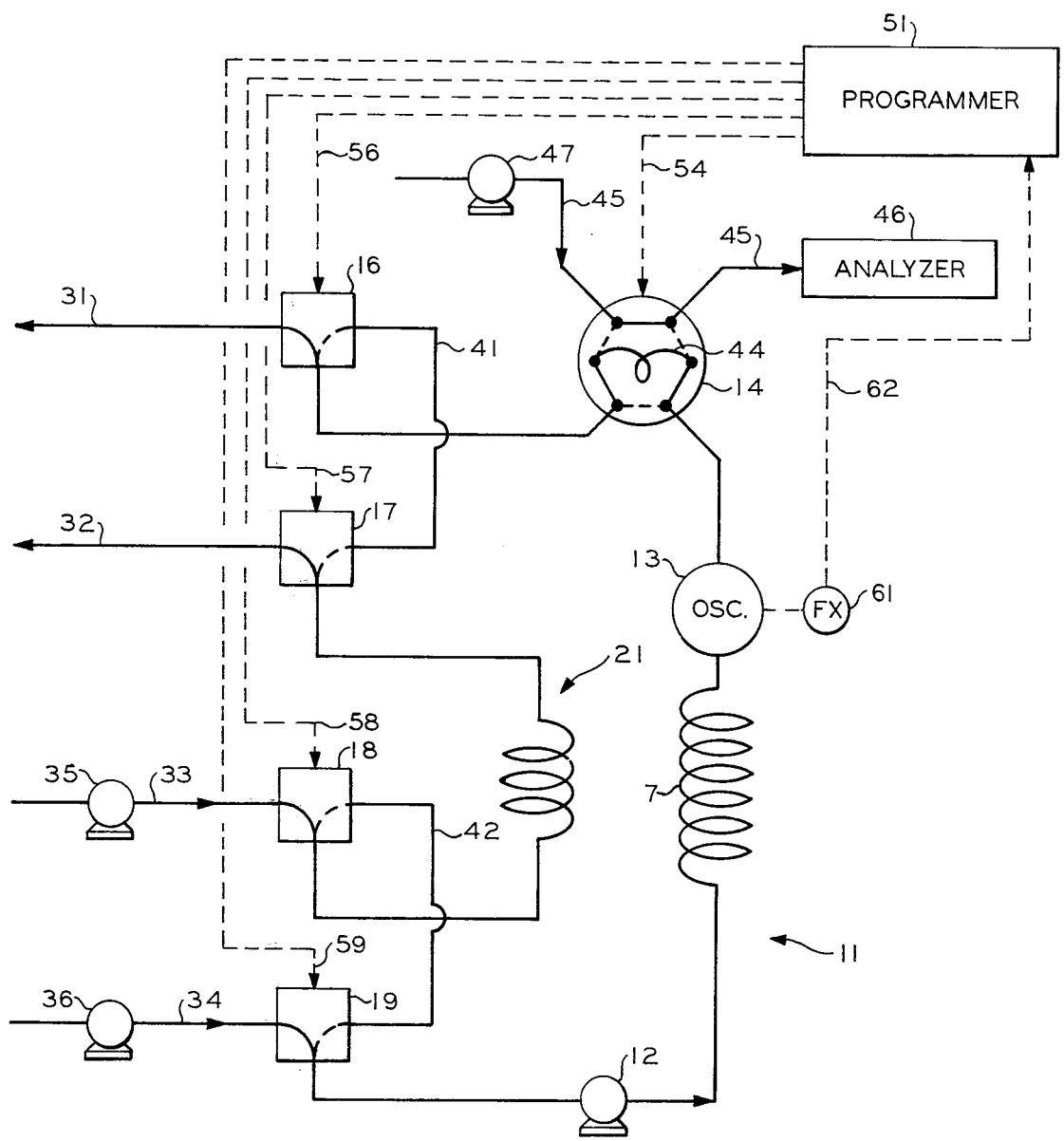
FIG. 1 is a schematic representation of a preferred sample dilution system embodying the apparatus and method of the invention.

Referring to FIG. 1 there is illustrated a first conduit means 11, including a pump means 12, a fluid oscillator means 13, and associated portions of a sample valve means 14, connected at its first end to a first valve means 16 and at its second end to a fourth valve means 19. A second conduit means 21 is connected at its first end to a second valve means 17 and at its second end to a third valve means 18. Each of the valve means 16, 17, 18, and 19 is a two-way valve permitting the establishment of fluid communication between the respective associated conduit end and either of two additional conduit means. Each of the valve means 16, 17, 18, and 19 therefore has a first position schematically illustrated in FIG. 1 by the solid line through the box representing the valve, and a second position schematically illustrated in FIG. 1 by the dashed line through the box representing the respective value.

When each of the valve means 16, 17, 18, and 19 is in its respective first position as illustrated by FIG. 1, the first valve means 16 establishes fluid communication between the first end of the first conduit means 11 and a diluent disposal conduit 31; the second valve means 17 provides fluid communication between the first end of the second conduit means 21 and a sample disposal conduit 32; the third valve means 18 provides for fluid communication between the second end of the second conduit means 21 and a sample supply conduit 33; and the fourth valve means 19 provides for fluid communication between the second end of the first conduit means 11 and a diluent supply conduit 34. When each of the valve means 16, 17, 18, and 19 is in its illustrated first position, therefore, diluent liquid flows through the diluent supply conduit 34, through the fourth valve means 19, and into the second end of the first conduit means 11. The diluent liquid then proceeds through the first conduit means 11 through the second end thereof, into the first valve means 16, and from the first valve means 16 into the diluent disposal conduit 31. At the same time, sample material flows through the sample supply conduit 33 and the third valve means 18 into the second end of the second conduit means 21, through the second conduit means 21 to the first end thereof, and then continues through the second valve means 17 into the sample disposal conduit 32. While the sample supply conduit 33 and diluent supply conduit 34 can be provided with appropriate pump means 35 and 36 respectively in order to insure a flow of sample material and diluent liquid to the third valve means 18 and fourth valve means 19 respectively, such pump means 35 and 36 or equivalent means for initiating flow through their respective supply conduits may not be necessary in applications where sufficient process or reservoir pressure is available to insure supply conduit flow. In addition, the pump means 12 located in the first conduit means 11 can be used under appropriate conditions to provide flow through the diluent supply conduit 34 and fourth valve means 19 into the first conduit means 11.

After a period of time sufficient for the flow of diluent material through the first conduit means 11 and sample material through the second conduit means 21 to displace and flush any material remaining from a previous dilution in either of the conduits through the associated disposal conduits 31 and 32 and for the first conduit means 11 and second conduit means 21 to be filled with fresh diluent liquid and sample material respectively, the valve means 16, 17, 18, and 19 are substantially simultaneously switched to their respective second positions. With the valves in their respective second position the first valve means 16 provides fluid communication between the first end of the first conduit means 11 and the first end of a first connecting conduit 41; the second valve means 17 provides fluid communication between the first end of the second conduit means 21 and the second end of the first connecting conduit 41; the third valve means 18 provides fluid communication between the second end of the second conduit means 21 and the first end of a second connecting conduit 42; and the third valve means 19 provides fluid communication between the second end of the first conduit means 11 and the second end of the second connecting conduit 42. In this configuration thefirst end of the first conduit means 11 and the first end of the second conduit means 21 are connected through the first connecting conduit 41, and the second end of the first conduit means 11 and second end of the second conduit means 21 are connected through the second connecting conduit 42 to provide a closed loop containing the diluent liquid of the first conduit means 11 and the sample material of the second conduit means 21. Continued actuation of the pump means 12 to provide continuing circuitous circulation of the contents of the closed loop containing the oscillator means 13 is then used to mix the contents of the closed loop unitl a uniformly diluted sample material mixture is obtained. Circulation through the closed loop can be maintained for as long as necessary to provide a uniformly diluted sample material mixture therein, with the exact time required for each specific apparatus configuration being dependent upon the relative volume of the loop, the speed and capacity of the pump means 12, the solubility and mobility of the sample material in the diluent liquid, the turbulence of flow through the conduit loop, and other similar parameters.

Although continued circulation around a conduit loop not containing a fluid oscillator means 13 can be used to dilute a sample, the use of a suitable fluid oscillator means 13 in accordance with the invention promotes rapid and thorough mixing of the sample material and diluent liquid to produce a uniformly diluted sample. The full characteristics of the fluid oscillator means 13 are such that a cyclic changing of flow rates and fluid pressures at one or more locations within the oscillator means 13 will be established by the flow of fluid therethrough at a frequency determined by the flow rate, density, and other similar physical characteristics of the fluid passing therethrough. The flow oscillation produced in this manner promotes the thorough mixing of the sample material and diluent liquid. While a great number of available fluid oscillating means 13 of varying specific configurations can be used in accordance with the invention, those oscillators best suited to provide efficient mixing of sample material and diluent liquid will be characterized by internal passageways of sufficient size to prevent any unacceptable impediment to flow caused by the presence of viscous sample materials which may be encountered. In addition, the best suited oscillators will contain no moving parts in order to insure continuing reliable unattended operation of the dilution apparatus. While the use of a single fluid oscillator means 13 is considered adequate to provide a substantial improvement in the mixing efficiency, the use of a plurality of such oscillators, either randomly selected and installed in the dilution system or coordinated to provide desired frequency and/or phase relationships which further promote sample and diluent mixing can be utilized.

In addition to providing flow oscillations which promote thorough mixing of the sample and diluent, the frequency of oscillation produced by the flow oscillator means 13 can be utilized to provide information relating to the nature of the fluid flowing therethrough due to the dependence of oscillator frequency on the physical characteristics of the fluid with which it is used. For example, a light liquid of low viscosity passing through a fluid oscillator will produce a higher frequency oscillation than would a material of high viscosity or greater density flowing through the oscillator at the same speed. Since many of the samples which can be advantageously diluted in accordance with the invention are characterized by high density and/or viscosity, and since many of the diluent liquids suitable for such dilutions are characterized by low densities and viscosities, monitoring of the frequency of oscillation produced by the fluids of the dilution system passing through the fluid oscillator means 13 can be used to determine the condition of the contents of the material from the dilution loop. For example, when the first conduit means 11 and second conduit means 21 are first connected and circulation of the combined contents of these conduit means around the resulting loop is initiated, the oscillation frequency of the fluid ocillator means 13 will be relatively high when substantially the pure diluent liquid is passing therethrough and will be relatively low when substantially undiluted sample material is passing therethrough. When dilution of a particular sample is begun, the oscillator frequency will exhibit alternate high and low values as the slugs of diluent liquid and sample material alternately pass therethrough. As the sample material is dispersed within the diluent liquid, however, these peaks will disappear. When the sample material has been uniformly diluted the oscillator frequency will become stable at a value between the high frequency characteristic of diluent alone and the low frequency characteristic of sample material alone. Monitoring of the frequency of the oscillator means 13 can therefore be utilized to determine the degree of completion of dilution and when the characteristic frequencies of diluent liquid alone and diluted sample material are sufficiently different, can also be utilized to monitor flushing of the first conduit means 11 in preparation for a subsequent sample dilution.

While the fluid oscillator means 13 can be placed at any desired location within either the first conduit means 11 or the second conduit means 21, location of the oscillator 13 within the first conduit means 11 is presently preferred in order to insure complete flushing of the oscillator 13 by fresh diluent liquid between successive dilution procedures and to permit beginning each dilution procedure with the fluid oscillator means 13 containing the less viscous of the two materials to be mixed.

The volumes of the first connecting conduit 41 and second connecting conduit 42 are preferably so much smaller than the volume of either the first conduit means 11 or second conduit means 21 that the minute amount of diluted sample material remaining therein from the immdiately preceding dilution procedure has an insignificant or negligible effect on the composition of any subsequent diluted sample. As a practical matter such connecting conduits 41 and 42 will ordinarily be no more than a coupling connecting one valve directly to another or, in any of the numerous equivalent apparatus configurations available, a short internal passageway in a double or multiple valve. However, in some applications such as the monitoring of process streams in which substantial rapid changes in sample material will not occur, the volume of the connecting conduits 41 and 42 can be greater, without causing any significant alteration of subsequent sample composition, than they can under similar circumstances in a process where it is important to immediately recognize small and rapidly changing variations in sample material content.

After a period of time sufficient for thorough mixing of the sample material and diluent liquid in the closed conduit loop, the sample valve 14 may be used to inject a preselected volume of sample material from the sample loop 44 thereof into the flow of chromatograhic carrier liquid through an analyzer input conduit 45 to a chromatographic analysis means 46. The analyzer input conduit 45 and analysis apparatus 46 can be any suitable liquid chromatographic analysis apparatus or, in the case of a sample which is diluted to provide increased volatility, could be a suitable gas chromatographic analysis apparatus in which the diluted sample material is vaporized to present a gaseous sample to the analysis means 46 for analysis. Although a pump means 47 is illustrated providing chromatographic carrier fluid flow, any suitable means for establishing such flow can be used.

In order to provide for automatic unattended dilution and sampling of sucessive portions of sample material, a suitable programming means 51 is provided to generate valve actuating signals 54, 56, 57, 58, and 59 to actuate respective valve means 14, 16, 17, 18, and 19 in a preselected timed relationship. As previously indicated, valve means 16, 17, 18, and 19 are preferably simultaneously changed from their illustrated first position (solid line) to their second position (dashed lines) in order to connect the first conduit means 11 and second conduit means 21 in a series relationship. While the sample valve means 14 is schematically illustrated in a first position (solid lines) wherein the sample loop 44 is included in the first conduit means 11, the size and characteristics of the sample loop 44 may be such that it is desirable to avoid passage of sample material therethrough until it has been completely diluted, and the sample valve means 14 may be maintained in its second position (dashed lines) until after sample material dilution has been accomplished.

When the complete dilution of the sample material has been accomplished and a uniform diluted sample material mixture is contained within the closed conduit loop, the sample valve means 14 is switched to its illustrated first position, if not already in that position, to permit the sample loop 44 to fill with the diluted sample material. After a period of time sufficient for the sample loop 44 to be flushed and filled with diluted sample material, the sample valve means 14 is placed in a second position to inject the sample contained within the sample loop 44 into the flow of material through the carrier conduit 45. After injection of the sample into the analysis system or other use of the diluted sample has been completed, all valves are returned to their initial position for initiation of a subsequent dilution cycle.

When the frequency of the fluid oscillator 13 is to be utilized to aid in controlling the operation of the dilution process and apparatus, a frequency transducer means 61 can be utilized to produce an oscillator frequency signal 62 representative of the frequency of fluid oscillation within the oscillator 13. The oscillator frequency signal 62 can then be transmitted to the programmer 51 where it can be used for any desired control purpose. For example, operation of a dilution system by the programmer 51 can be conducted in response to the various frequencies of oscillation resulting from the materials within the sample dilution loop, as previously discussed. In the alternative, the oscillator signal 62 can be used to supplement a fixed timed programmer sequence by initiating a predetermined delay in the sequence or flushing the dilution system and initiating dilution of a new sample or causing the generation of an alarm signal in response to one or more of various preselected conditions. Examples of such conditions would be the cessation of oscillation caused by plugging of the fluid oscillator, failure of the pump means 12, or other similar malfunctions within the dilution system; the presence of vapor in the liquid system; a change in flow rate attributable to an accumulation of residue within the dilution loop sufficient to affect the accuracy of the volume of diluent liquid or sample material provided to the dilution system; or other similar conditions for which characteristic oscillator frequency responses will be exhibited.

Figure 2:
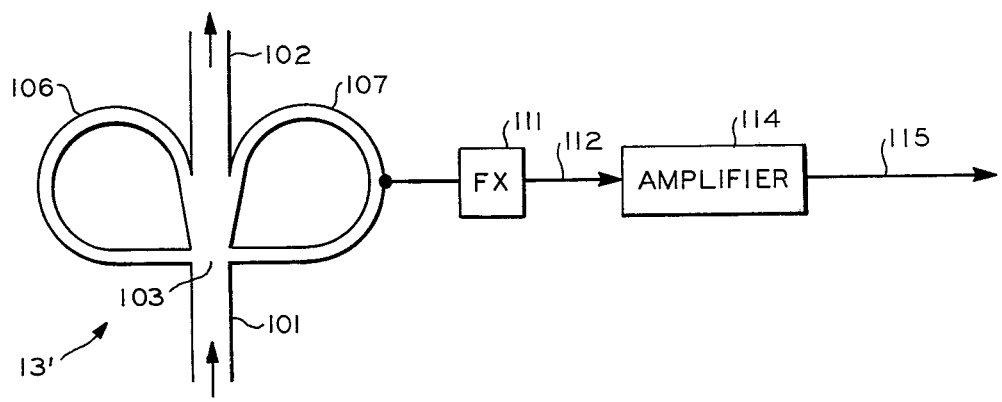
FIG. 2 is a schematic representation of a first embodiment of the oscillator of the invention.
Figure 3:
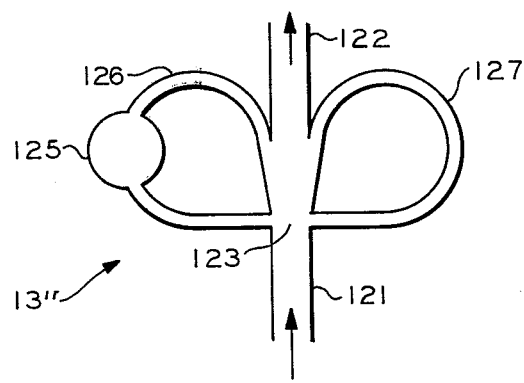
FIG. 3 is a schematic representation of a second embodiment of the oscillator of the invention.
Figure 4:
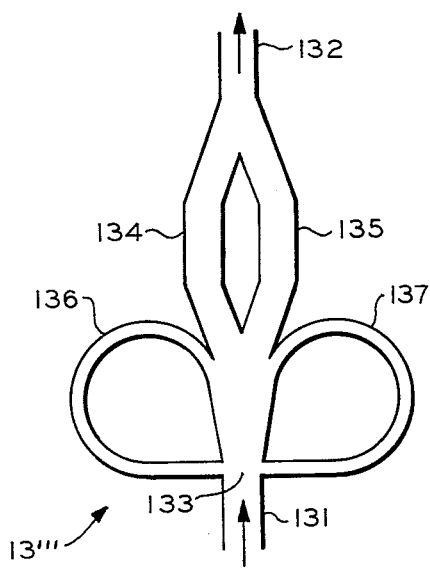
FIG. 4 is a schematic representation of a third embodiment of the oscillator of the invention.

Although, as previously indicated, a wide variety of fluid oscillator means 13 can be utilized in the practice of the invention, three possible fluid amplifier configurations are schematically illustrated by FIGS. 2-4. FIG. 2 illustrates a fluid oscillator 13' in which fluid is received from an inlet conduit 101 and diluted to an outlet conduit 102. A pair of proposed feedback conduits 106 and 107 provide a source of pressure and flow communication between their respective inlets adjacent the outlet conduit 102 and their respective outlets at the throat 103 of the oscillator adjacent the inlet conduit 101. In operation, rate of fluid pressure at the inlet of one of the feedback conduits, conduit 106 for example, causes an increased flow through the feedback conduit 106 with a corresponding increase in flow and pressure on its side of the oscillator throat 103 directing the flow through the inlet conduit 101 toward the inlet of the other feedback conduit 107. The increase in pressure at the inlet of the feedback conduit 107 and subsequent increase of flow through the feedback conduit 107 redirects the flow through the inlet 101 toward the inlet of the feedback conduit 106, and oscillation proceeds at a characteristic frequency determined by the flow rate, density, viscosity, and other similar physical characteristics of the fluid entering the inlet conduit 101 and contained within the feedback conduits 106 and 107 of the oscillator 13'.

Once oscillation is initiated, therefore, it is clear that it will be maintained by the continuing redirection of at least a portion of the fluid entering the oscillator through the inlet conduit 101. The initiation of oscillation as flow through the device is begun will ordinarily be accomplished by random pressure changes within the oscillator 13' or by either random or intentional variations in the flow characteristics of the feedback conduits 106 and 107.

The frequency of fluid oscillation within the oscillator 13' can be suitably monitored by means of a flow transducer 111 that to sense the changing flow rate within one of the feedback conduits 107 and produce a feedback conduit pressure signal 112 representative of that pressure. Since the cyclic oscillation of the oscillator 13' is directly reflected by the changing flow rate within the feedback conduit 107, the flow rate signal 112 will change in magnitude at a frequency representative of the frequency of oscillation within the oscillator 13'. A suitable flow transducer could employ a resistance bridge circuit employing a thermistor to sense the flow rate. An amplifier means 114 or other similar suitable apparatus can then be utilized to convert the flow rate signal 112 to a suitable oscillator frequency signal 115 which can be used for any desired purpose such as delivery to the programmer 51 of FIG. 1 as the oscillator frequency signal 62. Where the pressures and frequencies to be encountered are compatible, many other suitable frequency transducer means, such as, for example, a suitable pressure transducer or differential pressure transducer, can be employed.

In the oscillator 13" of FIG. 3, the inlet conduit 121, outlet conduit 122, oscillator throat 123, and feedback conduits 126 and 127 correspond functionally to their respective counterparts 101, 102, 103, 106 and 107 of the oscillator 13' in FIG. 2. In FIG. 3, however, enlarged conduit portion 125 having preselected volume and flow characteristics is incorporated into the feedback conduit 126 to alter the feedback characteristics of the conduit. The presence of such a feature will produce an effect generally analogous to the presence of a capacitor in the feedback portion of an electrical oscillator circuit. In the oscillator 13" illustrated by FIG. 3, the added cavity 125 can be used to create a desired imbalance between the feedback conduits 126 and 127. Such cavities can, however, be added to both feedback conduits of an oscillator to alter the frequency response of the device in such a manner as to provide oscillation at a desired frequency or within a desired frequency range or to "tune" the oscillator to perform advantageously in conjunction with other system components or characteristics.

The fluid oscillator 13''' of FIG. 4 utilizes an inlet conduit 131, an outlet conduit 132, an oscillator throat 133, and feedback conduits 136 and 137 which are analogous in their operation to the corresponding features 101, 102, 103, 106 and 107 of the oscillator 13' of FIG. 2. In addition to directing the flow at the throat 133 of the oscillator 13''', however, the feedback conduits 136 and 137 also initiate a division of flow of the fluid entering the inlet conduit 131 between downstream conduits 134 and 135. Using this configuration, increases in pressure and flow rate are through feedback conduits 136 and 137 are accompanied by corresponding increases in pressure and flow rate through the respective associated downstream conduits 134 and 135. The additional division and recombination of fluid flow when a separate downstream conduit is associated with each feedback conduit can be utilized to provide additional mixing efficiency within the oscillator 13'''. The downstream conduits 134 and 135 into which fluid flow is alternately directed by the effects of oscillation can be of the same length or can have differing lengths chosen to further promote the mixing effect initiated by the continuing redirection of flow between the two conduits as a result of the operation of the oscillator.

While the specific apparatus embodiment of the invention best suited for each particular application can vary widely, it has been found that for use with standard chromatographic analysis equipment the first and second conduit means 11 and 21 can advantageously be constructed from conduit having an inside diameter of at least about 0.2 inch (standard ¼ inch outside diameter tubing) when use of the system to dilute and lower the viscosity of a particularly viscous sample is desired. Likewise, it is preferred that the paths of fluid communication associated with the pumps and valves incorporated into the apparatus of the invention be large enough to permit the desired circulation of sample material and diluent liquid around the conduit loop to be maintained. If desired, a portion of either the conduit means 11 or conduit means 21, particularly the portion immediately downstream of the oscillator means 13, can be of a larger inside diameter than the remainder of these conduit means in order to promote more rapid mixing of the sample material with the diluent. Presently preferred apparatus for use in implementing the preferred embodiment of the invention for diluting a viscous rubber or polymer sample is as follows:

| | |
|---|---|
| Fluid oscillator means 13 | Fluidic Oscillator Catalog No. 19045 Fluidic Products Division Corning Glass Works 80 Houghton Park Corning, N. Y. 14830 |
| Remainder of first conduit means 11 | 1/4 in. O.D. 10 ft. long stainless steel |
| Second conduit means 21 | 1/4 in. O.D. 3 in. long stainless steel |
| Pump means 12, 35 and 36 | Gear pump model 17-51-303 Extraction Sampling Pump, mfg. by Micropump, 1035 Shary Court Concord, Calif. 94518 |
| Sample valve means 14 | High pressure model VIII mfg. by Applied Automation, Inc. Pawhuska Rd., Bartlesville, Okla. 74004 |
| Valve means 16, 17, 18, | Hoke valve No. 7663G4Y mfg. by |

| | |
|---|---|
| and 19 | Hoke Incorporated, Cresskill, N. J. |
| Conduit means 31, 32, 33, and 34 | Same size or larger than associated conduit means 11 and 21 |
| Pump means 47 | Model MCP-36 mfg. by Haskel Engineering and Supply Co., 100 E. Graham Place Burbank, Calif. 91502 |
| Connecting conduits 41, 42 | 1/4 in. O.D. (2–3 in.) stainless steel or short as possible |
| Carrier fluid supply conduit 45 | 1/16 in. O.D. stainless steel tube |
| Analyzer means 46 | Optichrom L/C liquid chromatographic analyzers sold by Applied Automation, Inc. |
| Programming means 51 | Model 102 sold by Applied Automation, Inc. |

Although the apparatus and method of the invention have been described herein in conjunction with a presently preferred embodiment thereof, it is to be understood that reasonable variations and modifications by those skilled in the art of sampling and analysis of various materials are within the scope of the foregoing description of the invention and of the appended claims thereto.

What is claimed is:

1. Apparatus comprising:
    first conduit means having a passageway therethrough with a first internal volume;
    second conduit means having a passageway therethrough with a second internal volume, said second internal volume having a predetermined size relationship to said first volume;
    fluid oscillator means, forming at least a portion of at least one of said first and second conduit means, for imparting flow oscillation to at least a portion of the fluid passing therethrough;.
    means for filling said passageway of said first conduit means with a diluent liquid;
    means for filling said passageway of said second conduit means with a sample material;
    means for connecting said passageway to said first conduit means and said passageway of said conduit means to form a closed conduit loop; and
    means for circulating said diluent liquid and sample material through said conduit loop to cause mixing thereof.

2. Apparatus in accordance with claim 1 wherein said oscillator means comprises feedback passageway means for periodically redirecting at least a portion of the fluid passing therethrough.

3. Apparatus in accordance with claim 1 additionally comprising means for detecting the frequency of oscillation produced by said fluid oscillation means.

4. Apparatus in accordance with claim 1 additionally comprising means for removing a preselected volume of diluted sample material from said conduit loop.

5. Apparatus in accordance with claim 1 wherein said means for circulating comprises a pump means.

6. Apparatus in accordance with claim 5 wherein said pump means is associated with said first conduit means.

7. Apparatus in accordance with claim 1 wherein said first and second conduit means comprise tubing having an inside diameter greater than about 0.2 inches.

8. Apparatus in accordance with claim 4 additionally comprising means for analyzing said preselected volume of diluted sample material removed from said conduit loop.

9. Apparatus in accordance with claim 1 wherein said fluid oscillator means is a part of said first conduit means.

10. Apparatus in accordance with claim 9 wherein said oscillator means comprises feedback passageway means for periodically redirecting at least a portion of the fluid passing therethrough.

11. Apparatus in accordance with claim 10 additionally comprising means for detecting the frequency of oscillation produced by said fluid oscillation means.

12. A method for diluting a sample, said method comprising:
    introducing a first preselected volume of a sample material into a first portion of a circuitous path;
    introducing a second preselected volume of a diluent liquid into a second portion of said circuitous path;
    circulating said sample material and diluent liquid around said circuitous path;
    producing flow oscillation in at least a portion of said circuitous path by passing the flow in said circuitous path through a fluid oscillator means forming a part of said circuitous path.

13. A method in accordance with claim 12 additionally comprising continuing circulating said sample material and diluent liquid until a desired degree of dilution is achieved.

14. A method in accordance with claim 13 additionally comprising generating a signal representative of the frequency of said flow oscillator 15. A method in accordance with claim 14 wherein introducing said second preselected volume of diluent liquid comprises introducing said diluent liquid into the portion of said circuitous path containing said fluid oscillator means.

16. A method in accordance with claim 12 wherein circulating said diluent liquid and sample material comprises continuously pumping the contents of said circuitous path in a preselected direction around said circuitous path.

17. A method in accordance with claim 16 wherein said sample material comprises a polymeric material.

18. A method in accordance with claim 16 wherein said sample material comprises a rubber material.

* * * * *

UNITED STATES PATENT AND TRADEMARK OFFICE
CERTIFICATE OF CORRECTION

PATENT NO. : 4,036,062
DATED : July 19, 1977
INVENTOR(S) : Charles G. Cruzan

It is certified that error appears in the above-identified patent and that said Letters Patent are hereby corrected as shown below:

Column 9, claim 1, line 40, after "passageway", change "to" to --- of ---.

Column 10, claim 14, line 47, after "flow" change "oscillator" to --- oscillation ---.

Signed and Sealed this

Twenty-sixth Day of June 1979

[SEAL]

Attest:

RUTH C. MASON
Attesting Officer

DONALD W. BANNER
Commissioner of Patents and Trademarks